United States Patent [19]
Hoyt et al.

[11] Patent Number: 4,777,819
[45] Date of Patent: Oct. 18, 1988

[54] UNTETHERED OCEANOGRAPHIC SENSOR PLATFORM

[76] Inventors: Joshua K. Hoyt, 26 Juniper Pt. Rd., Woods Hole, Mass. 02543; Albert M. Bradley, 160 Old Main Rd., N. Falmouth, Mass. 02556

[21] Appl. No.: 44,591

[22] Filed: Apr. 30, 1987

[51] Int. Cl.[4] .................... G01W 1/00; B63B 22/20
[52] U.S. Cl. .................................. 73/170 A; 441/2; 73/292
[58] Field of Search ............... 73/170 A, 864.31, 292; 114/326; 441/2, 28, 29; 374/136

[56] References Cited

U.S. PATENT DOCUMENTS

| | | | |
|---|---|---|---|
| 3,512,408 | 5/1970 | Douglass, Jr. | 374/136 X |
| 4,186,373 | 1/1980 | Thompson . | |
| 4,258,568 | 3/1981 | Boetes et al. | 73/170 A |
| 4,557,697 | 12/1985 | Kontar et al. | 441/2 |

OTHER PUBLICATIONS

Joshua K. Hoyt, *The Flying Fish, an Untethered Oceanographic Sensor Platform with Acoustic Homing Capability*, Woods Hole Oceanographic Institution and Massachusetts Institute of Technology Joint Program in Oceanography and Oceanographic Engineering Doctoral Thesis, WHOI-86-18, May 1986.
Hoyt, *The Fast Profiler*, Opportunity Brief #45, Marine Industry Advisory Services, MIT Sea Grant Program, Jul. 7, 1986. pp. 6–9.
*Speedy "Fish" Improves Oceanographic Data Collection*, The MIT Report, Nov. 1986, vol. XIV, No. 10, pp. 14–15.
Hoyt and Bradley, *The Fast Profiler*, presented at the Symposium on Unmanned Untethered Underwater Vehicles, University of New Hampshire, Jun. 1985.
Hoyt, *The Flying Fish: An Untethered Sensor Platform With Acoustic Homing Capability, Its Role In Global Scale Hydrographic Surveys*, presented at Oceans '85, San Diego, CA, 1985.

Primary Examiner—Charles A. Ruehl
Attorney, Agent, or Firm—Norman E. Brunell

[57] ABSTRACT

Method and apparatus for making depth related measurements from an untethered, gravity driven oceanographic platform. The platform is a smooth streamlined, torpedo shaped body releasably carrying ballast in its nose and covered with syntactic foam for buoyancy. At the appropriate depth, the ballast is released and the body ascends under control of an interferometric homing system which guides it to a recovery vessel. The ballast may be an iron slug held in place electromagnetically.

1 Claim, 3 Drawing Sheets

UNTETHERED OCEANOGRAPHIC SENSOR PLATFORM

BACKGROUND OF THE INVENTION

The present invention relates generally to an improved method and system for the use and deployment of an autonomous oceanographic instrument platform and particularly to such platforms useful for high speed excursions to and from great depths. Specifically, this invention relates to oceanographic instrument platforms used for conductivity, temperature and depth measurements (CTD), that is, conductivity and temperature measured as a function of depth. Such measurements are important in physical oceanography for measuring the circulation patterns of world oceans, in part, in order to improve meteorological and atmospheric models used to examine and predict weather conditions.

Conventional CTD measurements are made in situ from CTD sensors appended to data loggers lowered into the ocean depths on wires. Such systems are cumbersome and slow which makes them expensive for large scale operations. Their usefulness is also limited because the logging wire couples ship motion to the sensor platform which interferes with the measurement process. Other more complex instrument platforms have been developed for special purposes, but none satisfactorily provide an instrument platform useful for large numbers of easily launched and retrieved CTD or similar measurements at reasonable costs.

SUMMARY OF THE INVENTION

The present invention provides method and apparatus for making oceanographic measurements using an autonomous, streamlined, gravity driven oceanographic platform known as a "flying fish", capable of high speed vertical excursions from the surface to depths of 6000 meters. The flying fish uses a torpedo shaped body rendered positively buoyant with syntactic foam and ballasted negatively buoyant by the addition of an expendable slug of dense material. After dropping its ballast at depth, the flying fish guides itself to an acoustic beacon carried by a support ship at the surface by using a short baseline interferometer system in its nose.

BRIEF DESCRIPTION OF THE DRAWINGS

In the drawings wherein like reference numerals represent like parts:

FIG. 4 is a schematic illustration of flying fish 10 showing the relationship between the short baseline interferometers and the homing beacon.

DETAILED DESCRIPTION OF PREFERRED EMBODIMENT

FIG. 1

Figure 1:
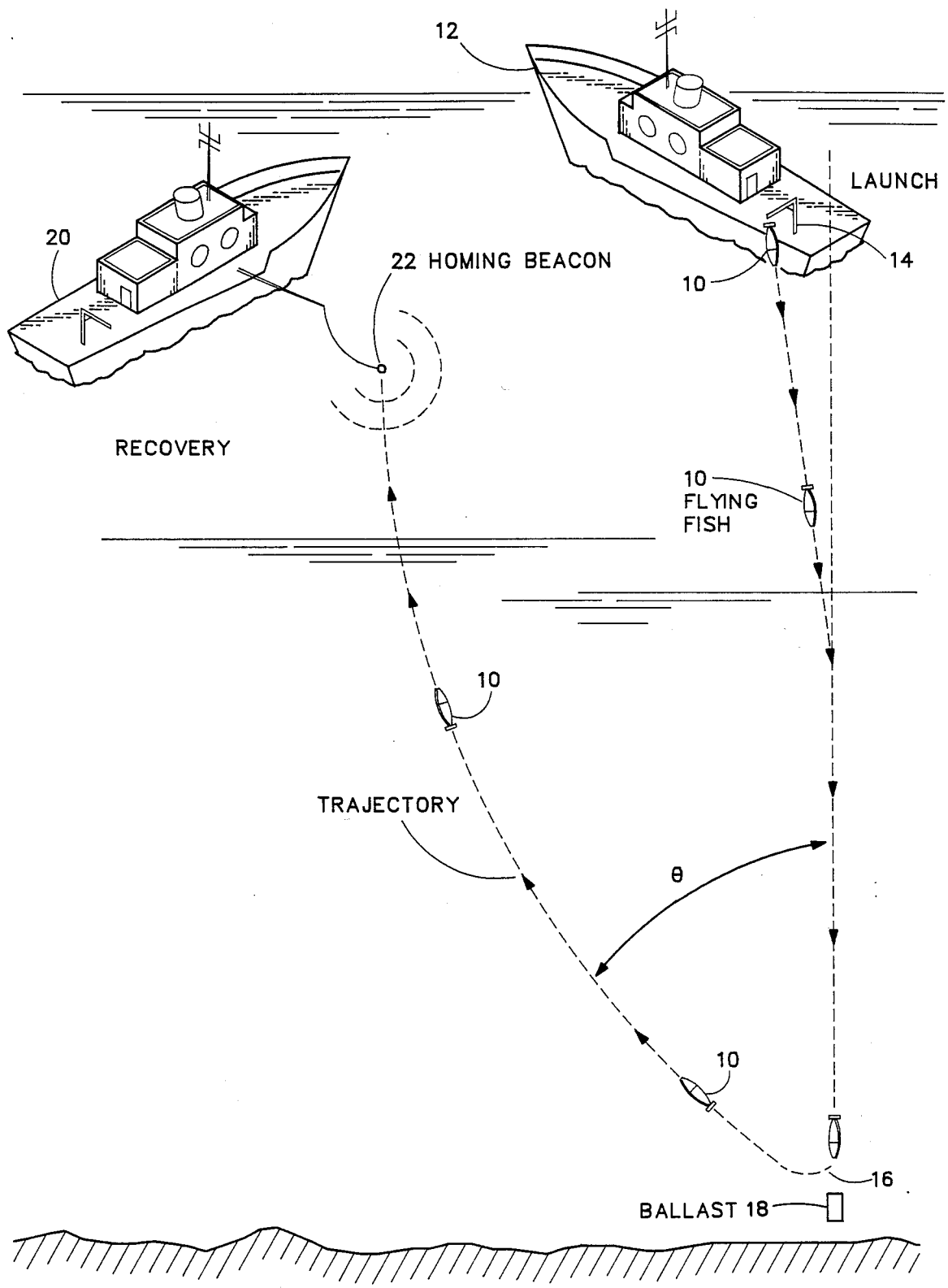
FIG. 1 illustrates the launch, descent, ballast drop, and ascent of the flying fish which may make CTD or other measurements at many different depths during its dive in accordance with a preferred embodiment of the present invention.

Referring now to FIG. 1, flying fish 10 is shown in position to be launched from conventional support 14 on surface ship 12. As described below in greater detail with respect to FIG. 2, flying fish 10 is ballasted negatively buoyant with ballast or weight 18 at launch. As indicated in this Figure, after launch flying fish 10 drops essentially vertically towards the ocean floor. During descent flying fish 10 serves as an oceanographic instrument platform carrying sensors, not shown, for making measurements, particularly CTD measurements useful in physical oceanography. Flying fish 10 is especially suited for multiple depth related measurements.

Near the bottom of its descent, shown in the Figure as descent point 16, flying fish 10 drops weight 18 and becomes substantially positively buoyant. As flying fish 10 ascends, it continues to serve as an oceanographic instrument platform. During ascent, flying fish 10 uses a short baseline interferometry, as described in more detail below with respect to FIG. 3, to steer towards homing beacon 22, positioned in the water near recovery vessel 20. Surface ship 12 may conveniently be used as recovery vessel 20.

FIG. 1 is not drawn to scale. Surface ship 12 and recovery vessel 20 are on the surface of the sea and descent point 16 may well be as much as 6000 meters below the surface. Trajectory angle $\theta$, the angle between the angle of ascent and the vertical, is designed to remain under about 10°. The physical construction of flying fish 10 may be understood in greater detail from the discussion below with regard to FIG. 2.

FIG. 2

Figure 2:
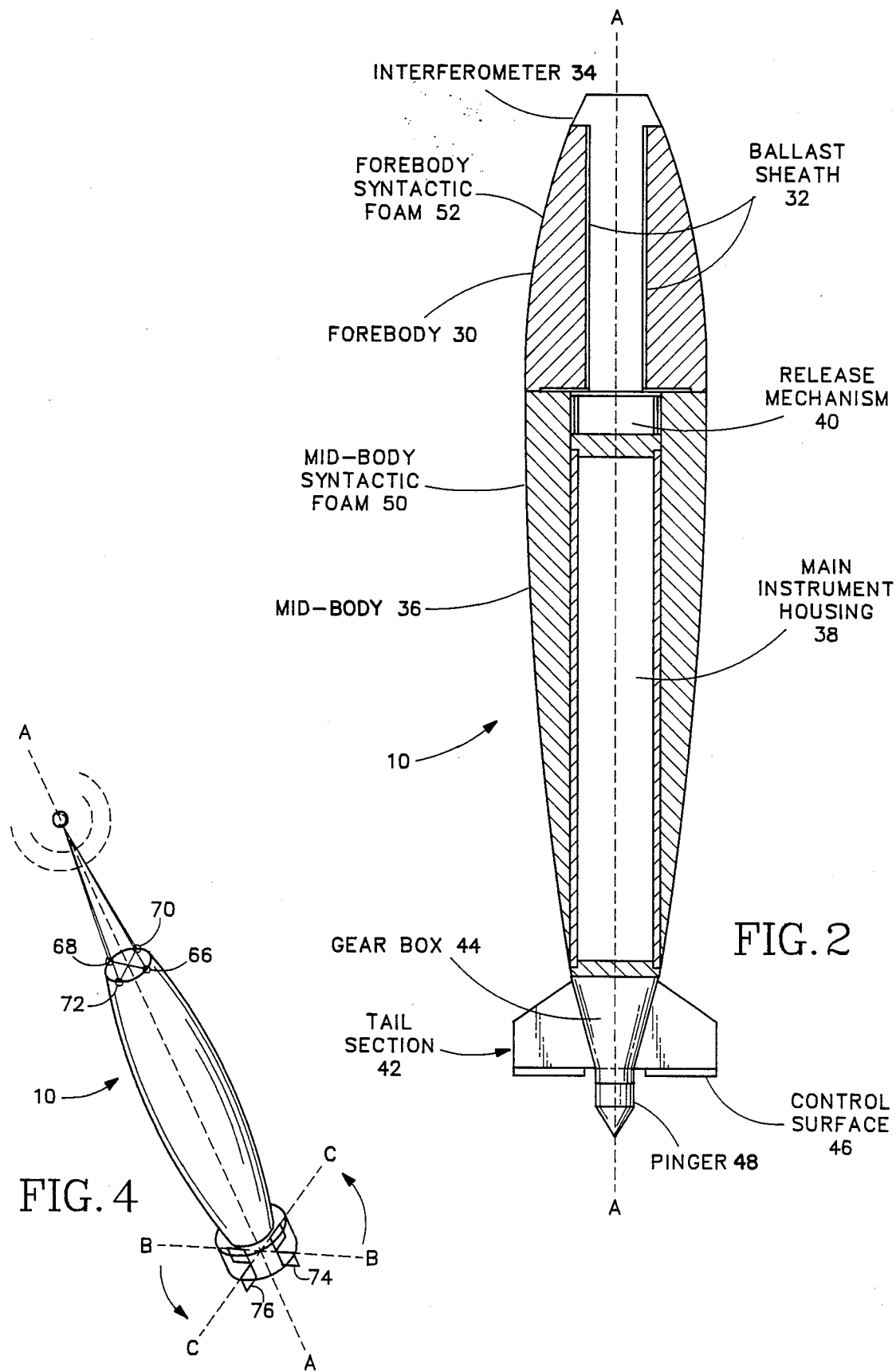
FIG. 2 shows a cut away view of flying fish 10, in accordance with the system shown in FIG. 1.

Referring now to FIG. 2, flying fish 10 has a streamlined, torpedo shaped body symmetrical about central axis AA. Flying fish 10 has three major body components: nose section or forebody 30 including ballast sheath 32 and interferometer system 34; mid-body 36 including main instrument housing 38 and ballast release mechanism 40; and tail section 42 including gear box 44, control surfaces 46 and pinger 48.

Main instrument housing 38 may conveniently be formed from a rigid, water-tight pipe of steel, aluminum, Fiberglas or titanium symmetrical about central axis AA forming the main structural backbone of flying fish 10. Gear box 44 is rigidly attached to one end thereof and ballast release mechanism 40 to the other. Ballast release mechanism 40 serves to capture the ballast, not shown, within ballast sheath 32, a central opening in forebody 30, until instructed to drop ballast by a signal from main instrument housing 38.

Interferometer system 34, described below in greater detail below with respect to FIG. 4, includes two pairs of hydrophones, in a plane perpendicular to central axis AA, forming orthogonally positioned short baseline interferometers for guiding flying fish 10 to homing beacom 22 during ascent.

Tail section 42 includes control surfaces 46 operated in response to interferometer system 34 to guide flying fish 10 during its vertical ascent toward homing beacon 22 on recovery vessel 20, as described below in more detail with respect to FIG. 4. Tail section 42 also includes electric motors, not shown, for operation of control surfaces 46 through gear box 44 which may be of conventional design. Pinger 48 is mounted at the rear of flying fish 10 on tail section 42 and serves to provide tracking and other information for recovery vessel 20 or surface ship 12 during deployment.

Flying fish 10 is rendered positively buoyant by an outer layer of syntactic foam which may conveniently be formed in two pieces: mid-body syntactic foam 50 and forebody syntactic foam 52. The foam forms an outer shell around most of flying fish 10 and serves to protect it, and the launch and recovery vessels, against physical damage during deployment.

Ballast release mechanism 40, mounted to main instrument housing 38 and in contact with the opening of ballast sheath 32, serves to release the ballast at descent point 16 and begin the ascent of flying fish 10 at a predetermined depth or under the command of surface ship 12 under specified conditions, such as the indicated malfunction of certain instrument systems. Ballast release mechanism 40 may be understood in greater detail with reference to FIG. 3 below.

FIG. 3

Figure 3:
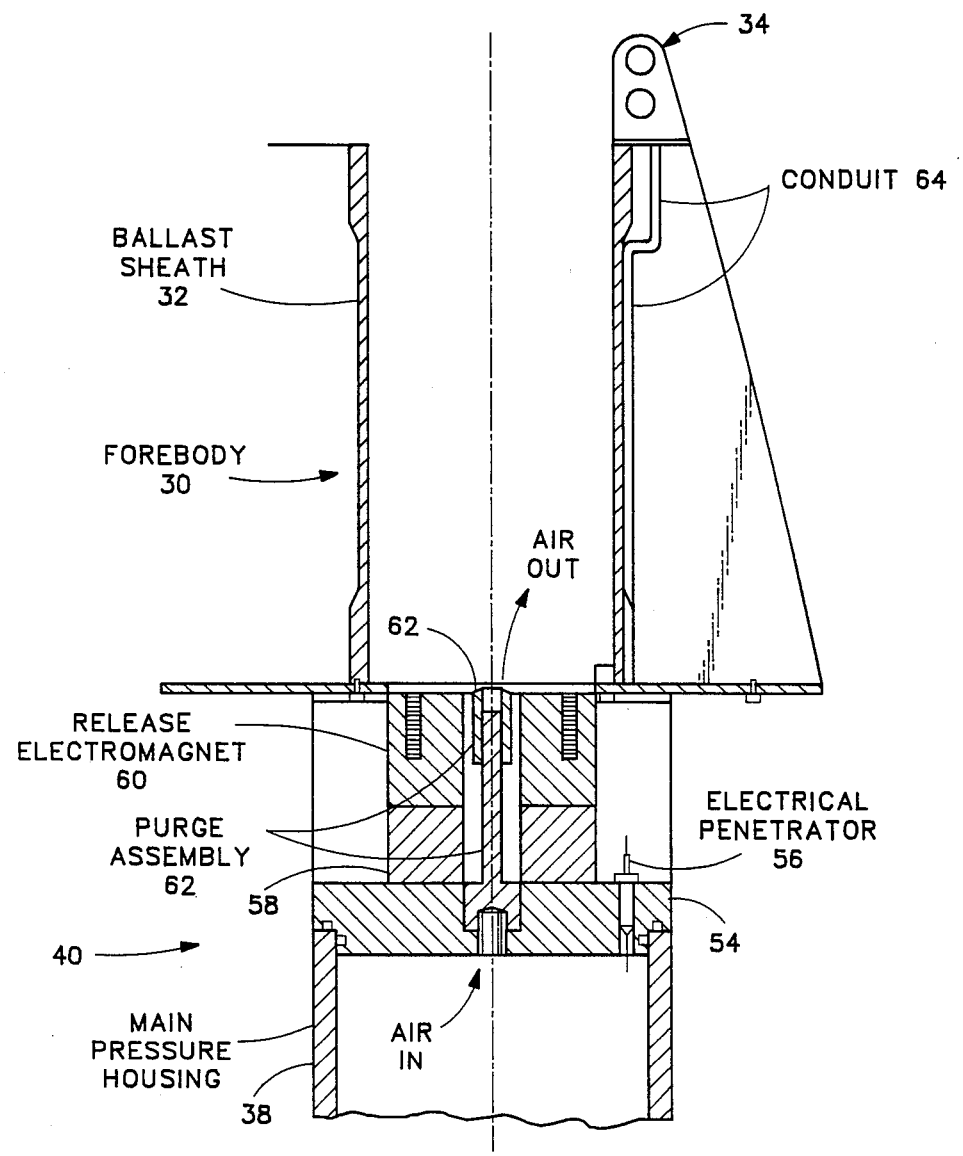
FIG. 3 is a partial cutaway view of the upper portion of flying fish 10 as shown in FIG. 2.

Referring now to FIG. 3, a portion of forebody 30 is shown in a cut away view, together with the details of ballast release mechanism 40 as well as the relevant portion of main instrument housing 38 in order to illustrate the relationship there between. Main instrument housing 38, which as described above may provide the main structural rigidity for flying fish 10, is sealed by a pair of end caps or other conventional pressure sealing mechanisms, such as end cap 54.

Electrical penetrator 56 provides the electrical power and signal paths between the instruments within main instrument housing 38 and ballast release mechanism 40 as well as interferometer system 34 and any other electrical devices outside of the protection of main instrument housing 38, such as electrical strobes, not shown, which are used for night operation.

Ballast release mechanism 40 includes mounting block 58 and release electromagnet 60 which serves to secure the ballast within ballast sheath 32. The ballast used must therefore be the appropriate size to fit within ballast sheath 32 loosely, provide sufficient negative buoyancy to overcome the positive buoyancy of flying fish 10 and provide the desired downward acceleration, and must have the right electromagnetic properties to permit release electromagnet 60 to hold it within ballast sheath 32 until released.

Alternate non-magnetic forms of ballast release may be used, but an electromagnetic system is preferred because such a system provides reliable and fail safe operation. That is, the ballast may easily be released upon detection of error or malfunction conditions, over depth or even if battery power becomes insufficient to retain it.

Ballast release mechanism 40 is penetrated along central axis AA by purge valve assembly 62 which may conveniently be used between deployments to vent any waste products out gassed from batteries during recharging or from other components within main instrument housing 38.

Interferometer system 34, positioned at the tip of forebody 30, includes four equally spaced hydrophones arranged as two orthogonal pairs of short baseline interferometers the operation of which is discussed below in greater detail with respect to FIG. 4. Interferometer system 34 is connected by electrical penetrator 56 to main instrument housing 38 through electrical conduit 64 which is protected from harm by syntactic foam.

FIG. 4

Referring now to FIG. 4, flying fish 10 is shown in schematic form in order to illustrate the operation of the interferometer system 34 which permits flying fish 10 to guide itself to homing beacon 22 suspended in the water near recovery vessel 20. Interferometer system 34 includes two orthogonal hydrophones pairs: hydrophones 66 and 68 forming one pair and hydrophones 70 and 72 forming the other. The hydrophones pairs are preferably symmetrically positioned about central axis AA in a plane perpendicular thereto.

The two short baseline acoustic interferometers formed with hydrophones 66, 68, 70 and 72 operate in a conventional and well known manner to determined homing information about the direction of ascent of flying fish 10 relative to a direct line to homing beacon 22. When central axis AA is aligned with a direct path to homing beacon 22, interferometer system 34 provides appropriate signals to main instrument housing 38 so that control surfaces 46 are positioned to maintain that course and control longitudinal rotation.

Any deviation therefrom is detected by one or both hydrophone pairs and causes an appropriate response from control surfaces 46. In particular, control surfaces 46 may conveniently include a pair of orthogonally mounted rudders: rudder 74 and rudder 76. Rudder 74 can be caused to rotate about rudder axis BB and rudder 76 can be caused to rotate about axis CC in order to control the heading of flying fish 10 about either axis, or both, during its ascent within trajectory angle $\theta$.

The guidance system of flying fish 10 may also be used to guide it to other transmitting beacons, perhaps at underwater locations. The system could be configured, for example, to direct flying fish 10 during descent towards a beacon positioned on the ocean and thereafter back to a recovery location.

We claim:

1. A method of making measurements from an untethered oceanographic sensor platform, comprising the steps of:

deploying a gravity powered, streamlined body carrying measurement sensors, the body being rendered negatively buoyant by ballast held electromagnetically in a ballast sheath at the nose of the body;

thereafter releasing the ballast therefrom causing the body to ascend;

receiving signals from a recovery location with a first pair of hydrophones mounted in the nose of the streamlined body in a plane perpendicular to a central axis thereof and with a second pair of hydrophones positioned in the plane along a line perpendicular to a line between the hydrophones of the first pair to form a pair of orthogonal, short baselines by interferometry to provide homing information related to that recovery location;

using the orthogonal baselines to operate control surfaces on the body to control the longitudinal rotation thereof and guide the body during ascent to the recovery location in accordance with the signals received; and making measurements while the body is at different depths.

* * * * *